United States Patent

[11] 3,933,805

Cohnen

[45] Jan. 20, 1976

[54] S(IV)-BENZO-1,2,4-THIADIAZINE COMPOUNDS AND PROCESS FOR THEIR PREPARATION

[75] Inventor: Erich Cohnen, Hamburg, Germany

[73] Assignee: Biersdorf, Akteingesellschaft, Hamburg, Germany

[22] Filed: Apr. 22, 1974

[21] Appl. No.: 462,593

[30] Foreign Application Priority Data

Apr. 30, 1973 Germany............................ 2321786

[52] U.S. Cl............................. 260/243 R; 424/246
[51] Int. Cl.².......................................... C07D 285/24
[58] Field of Search.................... 260/243 R, 243 D

[56] References Cited
UNITED STATES PATENTS 3,287,362  11/1966  Hurmer et al. ..................... 260/243

Primary Examiner—John M. Ford
Attorney, Agent, or Firm—Linda G. Bierman; Jordan B. Bierman; Kenneth J. Stempler

[57] ABSTRACT

S (IV)-benzo-1,2,4-thiadiazines having the structure

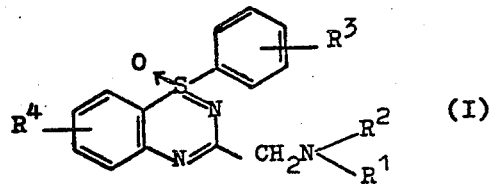

are disclosed. These compounds and their acid addition salts have been found to have anti-hypertensive and spasmolytic properties.

12 Claims, No Drawings

S(IV)-BENZO-1,2,4-THIADIAZINE COMPOUNDS AND PROCESS FOR THEIR PREPARATION

This application claims priority of German Pat. Application No: P 23 21 786.9 filed Apr. 30, 1973.

This invention relates to S (IV)-benzo-1,2,4-thiadiazines of the general formula (I)

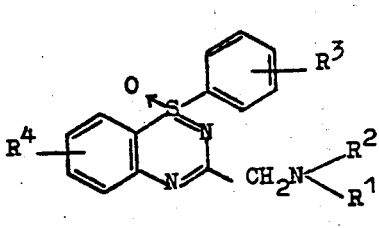

(I)

in which $R^1$ is hydrogen, lower alkyl or hydroxy lower alkyl; $R^2$ is lower alkyl, hydroxy lower alkyl, methoxy alkyl, or cycloalkyl; or $R^1$ and $R^2$, together with the nitrogen form a pyrrolidino, piperidino, hexamethylenimino or morpholino radical; $R^3$ is hydrogen, halogen, lower alkyl, nitro, or amino; and $R^4$ is hydrogen, halogen, lower alkyl, methoxy, or lower dialkylamino, as well as their physiologically tolerable acid addition salts. Lower alkyl means 1 to 4 carbon atoms; cycloalkyl means cyclopentyl or cylohexyl.

The new compounds of the present invention have valuable pharmacological properties. They show antihypertensive and spasmolytic effects as well as a depressing effect on the central nervous system. In mice, for example, they inhibit motor activity, prolong sleep induced by pentobarbital, and are anti-convulsive.

The substances can be used in their pure form, but it is preferred to use their acid addition salts which are easily crystallized. These compounds or their salts can be mixed with pharmacologically compatible substances such as vehicles and/or diluents of the usual kind. Hence, solutions for injection purposes and pharmaceutical preparations to be given orally, such as dragees, pills or tablets are within the scope of this invention.

The compounds of the general formula I can be produced by reacting 2-chloroacetamido-diphenyl sulfoxides of formula II

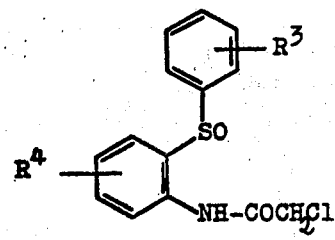

(II)

in which $R^3$ and $R^4$ have the above-stated meaning, with hydrazoic acid or its metal salts and a concentrated mineral acid, such as sulfuric. Preferably the reaction is conducted at a temperature of about 40° to 50° C. Simultaneous cyclization to the 3-chloromethyl-1,2,4-benzothia(IV)-diazine-1-oxides of formula III

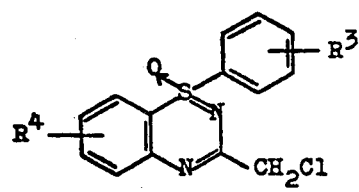

(III)

occurs. Subsequent reaction with a primary or secondary amine IV

(IV)

in which $R^1$ and $R^2$ have the above-stated meaning produces the compounds of general formula I. It has been found preferable to conduct this reaction at about 20° to 30° C.

The reaction of the compounds III with the amines IV to the substances of the invention is advantageously carried out in methanol with addition of dimethyl formamide at room temperature. The reaction times depend primarily on the amine used; they vary between a few hours and several days. The isolated oily bases are then dissolved in ethanol, and after addition of ethanolic hydrochloric acid, are converted into the well crystallizing dihydrochlorides - usually with inclusion of water of crystallization or alcohol.

Production of products of the general formula I in which $R^3$ is amino can be effected by reduction of the corresponding nitro compound with hydrogen and Raney nickel or palladium on charcoal catalyst.

The compounds of formula II are prepared by reacting 2-chloroacetamidodiphenyl sulfides with $H_2O_2$ in glacial acetic acid. The resultant sulfoxide is then precipitated by adding the reaction mixture to ice water.

The subsequent ring-closing reaction to the compounds of formula III is carried out preferably with sodium azide in a sulfuric acid-chloroform mixture at 40°–50°C. However hydrazoic acid and its other metal salts are also useable.

The present invention is further explained in the following Examples:

EXAMPLE 1

7-Chloro-3-di-(n-propyl)aminomethyl-1-phenyl-benzo-1,2,4-thiadiazine-1 oxide a. 5-Chloro-2-chloracetamido-diphenyl sulfoxide 93.6 g (0.3 mole) 5-chloro-2-chloracetamido-diphenyl sulfide, dissolved in 2 liters glacial acetic acid, are reacted drop by drop with 0.45 mole $H_2O_2$ (30%) at room temperature. The reaction solution is stirred for 18 hours at 25° and then dropped into ice water. The resulting sulfoxide is slightly contaminated with sulfone precipitates, but is used, after drying, without purification for the synthesis of the benzothiadiazine.

Melting point after recrystallization from ethanol: 130°-32°.

b. 7-Chloro-3-chloromethyl-1-phenyl-benzo-1,2,4-thiadiazine-1-oxide 84.0g (0.256 mole) 5-chloro-2-chloracetamidodiphenyl sulfoxide are dissolved in 1 liter $CHCl_3$, mixed with 650 cc concentrated sulfuric acid, and heated to 40° while stirring. To this mixture 33.3 g (0.512 mole)-$NaN_3$ is added incrementally such that the temperature does not exceed 50°. After completion of the addition, heating is continued for another 4 hours at 40°-50°. The product is left standing overnight, and the sulfuric acid phase is poured into 5 liters of ice water. The precipitating oil is extracted with $CHCl_3$. The $CHCl_3$ phase is dried with $MgSO_4$, concentrated, and recrystallized from ethanol. M.p. 128°-129°C.

c. 7-chloro-3-di-(n-propyl)aminomethyl-1-phenyl-benzo-1,2,4-thiadiazine-1-oxide 5g 7-chloro-3-chloromethyl-1-phenyl-benzo-1,2,4-thiadiazine-1-oxide and 20 g di-n-propylamine are dissolved in 80 ml methanol and left standing for 12 hours at room temperature. Thereafter the solution is evaporated and the residue distributed between chloroform and water. The chloroform phase is extracted with water several times, dried, evaporated, and the base (oil) dissolved in ethanol. After addition of ethanolic hydrochloric acid, the dihydrochloride precipitates. M.p. 192°-195° (decompn.).

EXAMPLE 2

3-Di-(n-propyl)-aminophenyl-1-(4'-aminophenyl)-benzo-1,2,4-thiadiazine-1-oxide 2.5 g of 3-di-(n-propyl)-aminomethyl-1-(4'-nitrophenyl)-benzo-1,2,4-thiadiazine-1-oxide (Example 17) are dissolved in 50 ml ethanol/water (1:1) and reduced under mild conditions with Pd/C. The catalyst is filtered off and the solvent drawn off under vacuum. The syrupy residue is dissolved in ehtanolic hydrochloric acid and concentrated. One obtains a highly hygroscopic substance. It is the dihydrochloride + $2H_2O$ having a melting point starting at 120°C (decompn.).

Analogously to Example 1, the following compounds are synthesized:

| Example No. | $R^1$ | $R^2$ | $R^3$ | $R^4$ | Melting point of the dihydrochloride C°(decompn.) | |
|---|---|---|---|---|---|---|
| 3 | —$(CH_2)_5$— | | H | 7—Cl | 205-10 | |
| 4 | $C_2H_5$ | $C_2H_5$ | H | 7—Cl | 208-11 | (½$H_2O$) |
| 5 | —$CH_2C$-$H_2O$— | $CH_2CH_2$— | H | 7—Cl | 190-5 | (½$H_2O$) |
| 6 | —$(CH_2)_4$— | | H | 7—Cl | 204-6 | (½$H_2O$) |
| 7 | H | $CH_2CH_2OH$ | H | 7—Cl | 182-5 | (½$C_2H_5OH$) |
| 8 | $CH_3$ | $CH_3$ | H | 7—Cl | 210-5 | (½$H_2O$) |
| 9 | H | $CH_2CH_2OCH_3$ | H | 7—Cl | 140-5 | (½$C_2H_5OH$) |
| 10 | $CH_3$ | $CH_2CH_2OH$ | H | 7—Cl | 170-5 | |
| 11 | —$(CH_2)_6$— | | H | 7—Cl | 125-30 | (½$H_2O$) |
| 12 | $CH_2CH_2OH$ | $CH_2CH_2OH$ | H | 7—Cl | 180-5 | |
| 13 | H | $C_2H_5$ | H | 7—Cl | 145-50 | ($C_2H_5OH$) |
| 14 | $CH_3$ | $CH_2CH_2OCH_3$ | H | 7—Cl | 180-85 | (½$C_2H_5OH$) |
| 15 | $CH_2CH_2CH_3$ | $CH_2CH_2CH_3$ | H | 6—$CH_3$ | 184-86 | |
| 16 | H | $CH_2CH_2OH$ | H | 6—$CH_3$ | 158-60 | ($C_2H_5OH$) |
| 17 | $CH_2CH_2CH_3$ | $CH_2CH_2CH_3$ | 4'—$NO_2$ | H | 164-5 | (½$H_2O$) |
| 18 | $CH_2CH_2CH_3$ | $CH_2CH_2CH_3$ | H | H | 198-200 | (½$H_2O$) |
| 19 | H | $CH_2CH_2OH$ | H | H | 178-80 | |
| 20 | $CH_2CH_2CH_3$ | $CH_2CH_2CH_3$ | 4'—Cl | H | 214-15 | (½$H_2O$) |
| 21 | H | $CH_2CH_2OH$ | 4'—Cl | H | 190 | |
| 22 | $CH_2CH_2CH_3$ | $CH_2CH_2CH_3$ | 4'—Cl | 7—Cl | 165-71 | ($H_2O$) |
| 23 | $CH_2CH_2CH_3$ | $CH_2CH_2CH_3$ | 3'—$CH_3$ | 7—Cl | 175-180 | (0,25 $C_2H_5OH$) |
| 24 | $CH_2CH_2CH_3$ | $CH_2CH_2CH_3$ | 4'—Cl | 8—Cl | 186-89 | |
| 25 | $CH_2CH_2CH_3$ | $CH_2CH_2CH_3$ | 4'—Cl | 7—$CH_3$ | 210-215 | |

Table 1

Central depressing effects in mice ($ED_{50}$ in mg/kg p.o.)

| Example No. | Decrease of spontaneous mobility[1] | Increase in Sleeping[2] | net[3] |
|---|---|---|---|
| 1 | 98 | 22 | 38 |
| 2 | >250 | 8,0 | |
| 3 | 84 | 34 | 34 |
| 4 | 78 | 46 | 28 |
| 5 | >250 | 46 | 92 |
| 6 | 70 | 38 | 68 |
| 7 | 23 | 15 | 126 |
| 8 | 96 | 16 | 46 |
| 9 | >250 | 58 | 32 |
| 13 | 240 | 25 | 42 |
| 14 | >250 | 28 | 46 |
| 15 | 76 | 8,5 | >500 |
| 18 | 186 | 3,1 | 134 |
| 19 | >250 | 2,0 | >500 |
| 20 | 31 | 2,0 | >250 |
| 21 | 46 | 9,0 | |
| 22 | 28 | 16 | |
| 24 | 16 | 20 | 115 |
| 25 | 31 | >250 | 21 |

(1) Method described in R.A. Turner, Screening Methods in Pharmacology, N.Y. 1965, p. 77.
(2) Prolongation of pentobarbital sleep, R.A. Turner, Screening Methods in Pharmacology, N.Y. 1965, p. 90.
(3) Minimum Electroshock Threshold, test arrangement according to Brown, Schiffmann, Swinyard and Goodman; J.Pharmacol. Exptl. Ther. 107, 273 (1953).

Table 2

Spasmolytic effect on guinea pig small intestine (1) in vitro against:

| Example No. | Acetylcholine (0.1 γ/ml) $ED_{50}$ (γ/ml) | Barium chloride (200 γ/ml) $ED_{50}$ (γ/ml) | Histamine (0.1 γ/ml) $ED_{50}$ (γ/ml) |
|---|---|---|---|
| 3 | 0,9 | 1,7 | 0,006 |
| 15 | 2,7 | 2,2 | 0,96 |
| 18 | 4,0 | 1,2 | |
| 20 | 2,6 | 0,051 | 0,019 |
| 22 | 2,2 | 0,72 | 0,027 |
| 23 | 1,1 | 0,9 | 0,08 |
| 24 | 2,2 | 0,72 | 0,04 |
| 25 | 0,69 | 0,69 | 0,003 |

(1) R. Magnus, Pflugers Arch. ges. Physiol. 102, 123 (1904)

What is claimed is:

1. An S (IV)-benzo-1,2,4-thiadiazine compound of the formula (I)

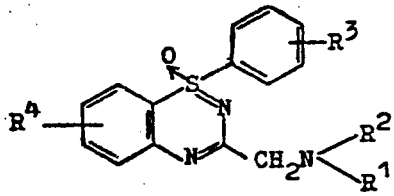

(I)

in which R¹ is hydrogen, lower alkyl or hydroxy lower alkyl; R² is lower alkyl, lower hydroxy alkyl, methoxy lower alkyl, cyclopentyl or cyclohexyl; or R¹ and R² together with the nitrogen to which they are attached form a pyrrolidino, piperidino, hexamethylenimino or morpholino radical, R³ is hydrogen, halogen, lower alkyl, nitro or amino; and R⁴ is hydrogen, halogen, lower alkyl, methoxy or diloweralkylamino; and physiologically acceptable acid addition salts of said compound.

2. The compound of claim 1 in which R³ is hydrogen, R⁴ is 7-chloro, and R¹ and R² together form a heterocyclic ring with the nitrogen atom to which they are attached and contain 4-6 carbon atoms.

3. The compound of claim 1 in which R³ is hydrogen, R⁴ is 7-chloro and R¹ and R² are both lower alkyl.

4. The compound of claim 1 in which R¹ is hydrogen, lower alkyl, or lower alkanol, and R² is lower alkyl, lower alkanol, or methoxy lower alkyl, R³ is hydrogen and R⁴ is 7-chloro.

5. The compound of claim 1 in which R³ is 4'-chloro or 3'methyl, R⁴ is hydrogen, 7- or 8- chloro or 7-methyl, and R¹ and R² are each n-propyl.

6. The compound of claim 1 in which R⁴ is 6-methyl, R³ is hydrogen, R¹ is hydrogen or lower alkyl and R² is loweralkyl or lower hydroxy alkyl.

7. The compound of claim 1 in which R⁴ is hydrogen, R³ is hydrogen 4'-chloro, 4'-amino, or 4-nitro, and R¹ is hydrogen, lower alkyl or lower hydroxy alkyl, and R² is lower alkyl or lower hydroxy alkyl.

8. The compound of claim 1 wherein R² is lower alkyl, lower hydroxy alkyl, methoxy ethyl or cycloalkyl; and R⁴ is hydrogen, halogen, lower alkyl or methoxy.

9. A process for the preparation of the compound of claim 1 which comprises reacting a 2-chloroacetamido-diphenyl sulfoxide having the structure (II)

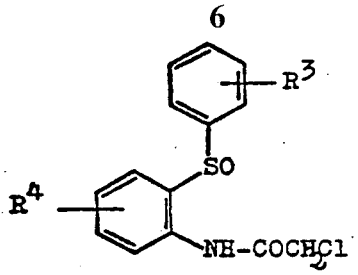

(II)

with hydrazoic acid or an alkali metal azide in the presence of a concentrated mineral acid to form a 3-chloromethyl-1,2,4-benzothia (IV) diazine-1-oxide intermediate having the structure (III)

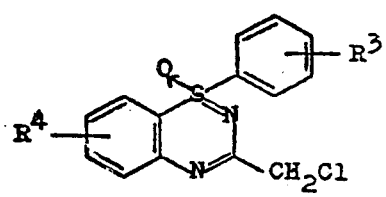

(III)

and reacting the intermediate with an amine having the structure

to form a reaction product.

10. The process of claim 9 in which compound II is reacted at a temperature of 40° to 50°C., the mineral acid is concentrated sulfuric, the azide salt is sodium azide, and compound III is reacted at a temperature of about 20° to 30°C.

11. The process of claim 9 in which R³ is a nitro group in compound III and the reaction product is further subjected to reductive hydrogenation to produce compound I in which R³ is an amine group.

12. The process of claim 9 in which R³ is a nitro group in compound III and the reaction product is further subjected to reductive hydrogenation to produce compound I in which R³ is an amine group.

* * * * *